(12) United States Patent
Vandroux et al.

(10) Patent No.: US 9,878,018 B2
(45) Date of Patent: Jan. 30, 2018

(54) COLLAGEN-BASED INJECTABLE PREPARATIONS CAPABLE OF CONTROLLING BLEEDING AND/OR OF SUBSTITUTING FOR PLATELETS IN THE CASE OF HAEMORRHAGIC SYNDROMES

(71) Applicants: NVH Medicinal, Dijon (FR); David Vandroux, Dijon (FR); Centre Hospitalier Universitaire De Dijon, Dijon (FR)

(72) Inventors: David Vandroux, Dijon (FR); Laure Dumont, Dijon (FR); Emmanuel De Maistre, Fontaine-les-Dijon (FR)

(73) Assignees: NVH Medicinal (FR); David Vandroux (FR); Centre Hospitalier Universitaire De Dijon (FR)

( * ) Notice: Subject to any disclaimer, the term of this patent is extended or adjusted under 35 U.S.C. 154(b) by 0 days.

(21) Appl. No.: 15/103,599

(22) PCT Filed: Dec. 11, 2014

(86) PCT No.: PCT/EP2014/077385
§ 371 (c)(1),
(2) Date: Jun. 10, 2016

(87) PCT Pub. No.: WO2015/086748
PCT Pub. Date: Jun. 18, 2015

(65) Prior Publication Data
US 2016/0310577 A1    Oct. 27, 2016

(30) Foreign Application Priority Data
Dec. 11, 2013 (FR) ..................... 13 62418

(51) Int. Cl.
| | |
|---|---|
| A61K 38/39 | (2006.01) |
| A61K 9/00 | (2006.01) |
| A61K 9/16 | (2006.01) |
| A61K 9/70 | (2006.01) |
| A61K 47/48 | (2006.01) |
| C07K 14/78 | (2006.01) |

(52) U.S. Cl.
CPC ............ *A61K 38/39* (2013.01); *A61K 9/0019* (2013.01); *A61K 9/1658* (2013.01); *A61K 9/70* (2013.01); *A61K 47/48215* (2013.01); *A61K 47/48246* (2013.01); *A61K 47/48876* (2013.01); *C07K 14/78* (2013.01); *C07K 2319/21* (2013.01)

(58) Field of Classification Search
None
See application file for complete search history.

(56) References Cited

U.S. PATENT DOCUMENTS

| 2009/0299034 A1 | 12/2009 | Cejas et al. | |
| 2011/0207669 A1* | 8/2011 | Vandroux | C07K 14/001 514/14.9 |
| 2015/0276762 A1* | 10/2015 | Vandroux | G01N 33/6893 435/7.92 |

FOREIGN PATENT DOCUMENTS

| WO | 98/57678 A2 | 12/1998 |
| WO | 2014/06058 A1 | 1/2014 |

OTHER PUBLICATIONS

Freitas, Robert A., "Cytometrics" Nanomedicine, vol. I (1999) available online at http://www.nanomedicine.com/NMI/8.5.1.htm.*
The GenBank entry ETE64774.1, downloaded Jan. 5, 2017.*
Sturk, Augueste et al, "Platelet activating factor: mediator of the third pathway of platelet aggregation." J. Clin. Ivest. (1987) 79 p. 344-350.*
Asselin, Judith et al, "Monomeric (glycine-proline-hydroxyproline)10 repeat sequence is a partial agonist of the platelet collagen receptor glycoprotein vi." Biochem. J. (1999) 339 p. 413-418.*
Cheng, Shanmei et al, "How sequence determines elasticity of disordered proteins." Biophys. J. (2010) 99 p. 3863-3869, p. 3866.*
Barnes, Alexander B. et al, "Resolution and polarization distribution in cryogenic dnp/mas experiments." Phys. Chem. Chem. Phys. (2010) 12 p. 5861-5867.*
Tojo, Akihiro and Kinugasa, Satoshi, "Mechanims of glomerular albumin filtration and tubular reabsorption." Int. J. Nephrol. (2012) article ID 481520.*
Memo from Dec. 29, 2005 from the directors of TC1600.*
An B et al. Frontiers in chemistry. Jun. 2, 2014; article 40.
Beynon C et coll. Crit Care. Jul. 26, 2012;16(4):228.
Bonhomme F et coll. Eur J Intern Med. 2014, 25(3):213-20.
Clementson K. ThrombosisResearch 2012 129 220-224.
Fries D. Transfusion 2013; 53:91S-95S.
Geutjes P J et al "Preparation and charcterization of injectable . . . " Journal of Vascular Surgery 2010 MOSBY vo. 52027442941, No. May 11, 2010, p. 1330-1338.
Herr et AL "Sutructural Insights . . . " Journal of Biological Chemistry, Vo. 284, No. 30, Jul. 24, 2009, p. 19784-19785.
Jenkins DH et coll. Shock. May 2014;41 Suppl 1:3-12.
Kar et coll. Jounal of Biological Chemistry 2006 vol. 281, n°44 33283-33290.
Kojima C et coil J. Am. Chem. Soc. 2009 131, 30652-6053.
Lashof-Sullivan M et coll. Nanoscale 2013, 5, 10719-10728.
Lisman Ton et al: "A single high-affinity binding site for von Willebrand . . . " Blood, American Society of Hematology, US, vo. 108, No. 12, Jan. 12, 2006 p. 3753-3756.
Mazepa M et coll. ATVB 2013, 33(8) :1747-52.
Modery-Pawlowski C et coll. Biomaterials 2013: 516-541.

(Continued)

*Primary Examiner* — Fred H Reynolds
(74) *Attorney, Agent, or Firm* — Banner & Witcoff, Ltd.

(57) ABSTRACT

The present invention relates to an injectable preparation comprising particles or fibrils with length less than 10 μm and at least one pharmaceutically acceptable vehicle or excipient. The particles or fibrils comprise proteins or peptides inducing adhesion and activation of the platelets, or even aggregation thereof. The preparation is useful for treating hemorrhages.

9 Claims, 8 Drawing Sheets

(56) References Cited

OTHER PUBLICATIONS

Murdock AD et coll. Shock. May 2014;41 Suppl 1:62-9.
Pires M et Chmielewski J. J. Am. Chem. Soc. 2009 131, 2706-2712.
Przybyla D et coll. J. Am. Chem. Soc. 2013, 135, 3418-3422.
Slatter D et coll. Peptides 2012 36, 86-93.
Spahn D et coll. Critical Care 2013, 17:R76.

* cited by examiner

A

| Conditions | Quantity of collagen injected | % PE | Mean Time |
|---|---|---|---|
| CONTROL n=5 | | 0% | > 15min |
| COLL type I n=5 | 400 µg/kg | 100% | 5 min 50 |
| Seq ID No. 1 n=4 | 1 mg/kg | 0% | > 15min |

B

A: Control
B: Seq. ID No. 1 (1 mg/kg)
C: Coll type I (400 µg/kg)

8A

8B

COLLAGEN-BASED INJECTABLE PREPARATIONS CAPABLE OF CONTROLLING BLEEDING AND/OR OF SUBSTITUTING FOR PLATELETS IN THE CASE OF HAEMORRHAGIC SYNDROMES

FIELD OF THE INVENTION

The invention relates to a collagen-based injectable preparation for its use in the treatment of hemorrhages. The injectable preparation consists of proteins and peptides derived from collagen capable on their own of inducing both adhesion and activation of platelets, and even their aggregation. The present invention also relates to the emergency injection by the systemic/general route of proteins and peptides derived from collagen into patients treated with antiplatelet drugs in an emergency situation (hemorrhage, surgical operation).

BACKGROUND OF THE INVENTION

Hemorrhage is defined as a flow of blood outside of the normal bloodstream. It can consist of simple bleeding or become massive in certain situations, notably trauma, and lead to a state of hemorrhagic shock associated with a drop in blood pressure.

Various clinical contexts lead to a risk of hemorrhage, such as surgery, trauma, treatment, thrombocytopenia or a constitutional or functional deficiency (such as hemophilia) (Spahn D et al. *Critical Care*. 2013, 17:R76). In severe hemorrhaging, coagulopathy is observed. The coagulopathy corresponds to the consumption of platelet and coagulation factors. Treatment is essential and the result of the hemorrhage depends on it. Various treatment strategies are currently followed.

One approach consists of using a transfusion support based on fresh frozen plasma (FFP), packed red blood cells or platelets. Nevertheless, the success of the platelet-based approach is limited by several factors, including the accessibility of platelets, their short shelf life (5 days on average), problems related to the conditions of storage, the risk of contamination of certain types of sample, their cost and the risk of inefficacy or even intolerance due to alloimmunization.

Another approach is based on the use of coagulation factor concentrates, such as fibrinogen concentrates and prothrombin complex concentrates (factors II, VII, IX and X). Studies have also suggested the use of factor VIIa (NovoSeven®). However this last use is not recommended because of the high rate of induced thrombosis.

Finally, another approach in emergency situations consists of using tranexamic acid, which is a powerful plasminogen activation antagonist and so acts as an antifibrinolytic (Fries D. *Transfusion*. 2013; 53:91S-95S).

None of the approaches proposed to date enables induction of platelet activation and aggregation during a hemorrhagic episode, although these are key steps in stopping bleeding. When a vascular injury leads to bleeding, a series of steps, referred to as primary hemostasis, is put in place. It involves the platelets, biconvex disk-shaped cells without nuclei approximately 2-5 µm in diameter. Various actors participate in this process, which leads to the formation of a hemostatic clot. The first phase, called adhesion, enables the recruitment of circulating platelets at the site of injury. This step involves the Willebrand factor, collagen and platelet receptors called collagen receptors (GpVI and $\alpha 2\beta 1$). The second phase, called platelet activation, comprises the liberation of pro-aggregant factors and the expression on the platelet surface of proteins such as P-selectin. This phase is followed by the phase called aggregation, which notably involves fibrinogen and the platelet receptor GpIIb/IIIa and the membrane exposure of procoagulant phospholipids enabling the fixation of coagulation factors to the site and eventually the formation of a fibrin/platelet clot and the stopping of bleeding.

It is now well established that the activation of platelets during the process of hemostasis leads to the appearance of two populations of platelets, called pro-aggregant and pro-coagulant. The latter are characterized by the surface expression of phosphatidylserine, at the origin of thrombin generation. These are called superactivated platelets. Hence we speak of platelet superactivation potential to describe the capacity of each individual to generate this population of platelets in response to agonists such as thrombin and collagen. Recent studies suggest that any therapeutic strategy aiming to induce the appearance of this population of activated platelets shows great potential for the treatment of hemorrhagic situations (Mazepa M et al. *ATVB* 2013, 33(8): 1747-52). Furthermore, their interest is reinforced by data confirming that the hemostatic effect of transfused platelets is dependent on this population. However, the approaches proposed to date are not based on the injection into the bloodstream of physiological or natural platelet activators such as collagen or proteins and peptides derived from collagen claimed in the present invention.

The central role of platelets in stopping bleeding is at the origin of recent work aiming to develop products derived from or mimicking platelets (synthetic platelets). Among the approaches proposed, there is a distinction between those based on products derived from cells, such as thromboerythrocytes and thrombosomes, and those using micrometer-sized particles covered with peptides derived from proteins involved in the platelet activation cascade, such as synthocytes or Fibrocaps™ based on peptides derived from fibrinogen (RGD peptides or dodecapeptide H12), or those covered with peptides binding to Willebrand factor, to collagen and to GpIIb/IIIa (Lashof-Sullivan M et al. *Nanoscale* 2013, 5, 10719-10728). A hemostatic effect has been described for these particles covered with peptides binding to Willebrand factor, to collagen and to GpIIb/IIIa, which enables an application to be envisaged in the hemorrhagic context. However, this approach poses a major problem of industrialization for this type of product, which combines several peptides on a single particle, with the necessity to master and qualify parameters such as the rate of binding and the ratio for each of the peptides, as well as the stability of the product once injected, without considering the fact that very high doses (of the order of several tens of milligrams per kilogram) must currently be injected (Modery-Pawlowski C et al. *Biomaterials* 2013:516-541).

There is therefore a need for new means of treatment of hemorrhage that are injectable into the bloodstream to be made available. Preferably these would be easily prepared industrially and able to be used at low concentrations.

With the aging of the population, physicians are more and more frequently confronted with patients treated with anticoagulants and antiplatelet drugs. Although the strategy of temporary withdrawal of these treatments is well-defined for programmed interventions (5-7 days' withdrawal for new antiplatelets drugs and 5 days' withdrawal for new anticoagulants), they seriously complicate the emergency treatment of patients in hemorrhagic situations (surgery or trauma, notably cranial) (Bonhomme F et al. *Eur J Intern Med.* 2014 March; 25(3):213-20). Various strategies of emergency reversion have been proposed but, for the new antiplatelet drugs, these are mostly limited to transfusion of platelets (Beynon C et al. *Crit Care.* 2012 Jul. 26; 16(4): 228). There is a need for new injectable hemostatic products that are capable of enabling recovery of platelet function during hemorrhagic episodes independently of the mode of action of these new antiplatelet drugs. The fact that the collagen-dependent platelet activation pathway is the most physiological, and is not, to date, modified by any antiplatelet treatment on the market, reinforces the interest of administering proteins or peptides derived from collagen by the systemic route in these situations. It is well established that the binding of GPVI to collagen or the proteins or peptides derived from collagen of the present invention leads to intense signaling within the platelets.

In a logistically constrained context, such as overseas theaters of military operations, the treatment of hemorrhage is governed by the concept of "damage control resuscitation", notably involving transfusion (packed red blood cells, plasma and platelets). Nevertheless, this situation is characterized by a difficulty of access to these blood products, especially to platelets, requiring an modified treatment, covered by the term "remote damage control resuscitation", with the use of whole blood as the principal difference (Jenkins D H et al. *Shock.* 2014 May; 41 Suppl 1:3-12). This strategy, although associated with a risk of contamination, is promising but remains limited to the military domain at present (Murdock A D et al. *Shock.* 2014 May; 41 Suppl 1:62-9).

The present invention relates therefore to the interest of intravenous administration of platelet-activating proteins or peptides derived from collagen as a new injectable hemostatic in three situations involving hemorrhage:
  during an episode of massive bleeding, notably non-compressive, requiring the ability to activate the platelets in the bloodstream;
  as an adjuvant during transfusional resuscitation away from a medical center, as a complement to an approach based on the transfusion in particular of whole blood or platelets;
  as a reverting agent for new antiplatelet drugs (e.g. prasugrel, ticagrelor), which are currently on the market without antidotes, for surgery or hemorrhage, notably intracranial.

SUMMARY OF THE INVENTION

The present invention relates to an injectable preparation for its use in the treatment of hemorrhages including:
  particles or fibrils of length less than 10 μm, such particles or fibrils proteins or peptides inducing the adhesion and activation of platelets, or even their aggregation; and
  at least one pharmaceutically acceptable vehicle or excipient.

SUMMARY OF THE DRAWINGS

FIG. 7A shows the results obtained on the mortality of mice after injection and FIG. 7B shows the biodistribution of macroaggregates of albumin radiolabeled with technetium injected at least 5 minutes after the administration of the various collagens tested.

DESCRIPTION OF THE SEQUENCES

Figure 1:
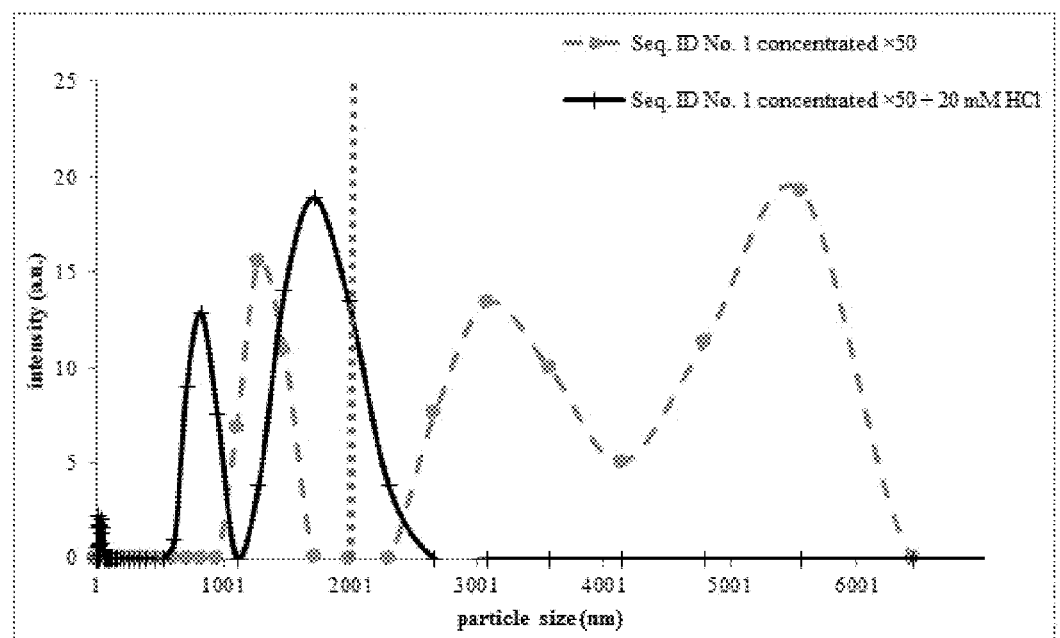
FIG. 1 shows the measurement by DLS of the size of the particles of a protein extract of the polypeptide of sequence ID No. 1 after concentration by a factor of 50.

Sequence ID No. 1: polypeptide coding for a recombinant protein capable of inducing the adhesion and activation of platelets.

DETAILED DESCRIPTION OF THE INVENTION

The present invention relates to an injectable preparation for its use in the treatment of hemorrhages comprising:
  particles or fibrils having a length less than 10 μm, said particles or fibrils comprising proteins or peptides inducing the adhesion and activation of platelets; and
  at least one pharmaceutically acceptable vehicle or excipient.

The injectable preparations according to the present invention enable platelet activity to be stimulated. In certain embodiments, the particles or fibrils include proteins or peptides that induce the adhesion and activation of platelets and also the aggregation of platelets once injected into the bloodstream. The latter can also be used as an adjuvant to pre-activate the platelets during transfusion of platelet concentrates or whole blood.

Proteins or Peptides Inducing the Adhesion, Activation, and Even Aggregation of Platelets The proteins or peptides entering into the formulation of the preparations of the present invention have the capacity to induce both adhesion and activation of platelets, or also the aggregation of platelets. It should be understood that these two or three activities are properties of one and the same protein or peptide. These proteins or peptides are in the form of particles or fibrils having a length less than 10 μm.

Preferably the fibrils have a length less than 9 μm, 8 μm, 7 μm, 6 μm, 5 μm, 4 μm, 3 μm, 2 μm, 1 μm or 0.5 μm. More preferably the fibrils have a length of between 0.5 and 9 μm, between 1 and 5 μm or between 2 and 4 μm.

These proteins or peptides are capable of binding, or of activating, the Willebrand factor, responsible for the adhesion of platelets, and of inducing the surface expression of P selectin or of phosphatidylserine, markers of platelet activation. In certain embodiments, the proteins or peptides are capable of inducing in vitro the aggregation of a plasma rich in platelets or of whole blood.

In certain embodiments, the proteins or peptides can stimulate the platelets and induce the stopping of bleeding without necessarily being capable of inducing the activation of coagulation, which is dependent on the expression of phosphatidylserine on the surface of the platelets, the formation of a surface said to be procoagulant, and the resulting generation of thrombin. This enables the risk of thrombosis induced after a systemic injection of the preparation to be limited. The activation of this subpopulation of activated platelets, called procoagulant platelets, can nevertheless occur but at levels below those necessary for the generation of thrombin detectable by classic tests.

A family of proteins, called collagens, have the capacity to induce the three aforementioned activities due to the presence in the sequence of certain collagens, principally collagens of types I and III, of peptide sequences capable of binding to circulating Willebrand factor and to two platelet receptors, GpVI and α2μ1. This leads to the adhesion of platelets, to their activation and then to their aggregation. In this way, the proteins entering into the formation of the preparations of the present invention may be chosen from among the collagens, and in particular the collagens of types I and III.

To date, the use of collagen to treat hemorrhages has not been proposed. This can be explained by the fact that, of the native collagens, only those in fibrillar form are described as capable of inducing adhesion, activation and aggregation of platelets (Clementson K. *Thrombosis Research* 2012 129 220-224). However, this fibrillar form, with fibres that can reach several micrometers in length, is not compatible with injection into the bloodstream. The specific forms of the present invention are compatible with injection into the bloodstream.

Specific forms of collagen, such as microspheres, microflorettes and dendrimers, can be obtained by methods such as those described by Pires M and Chmielewski J. *J. Am. Chem. Soc.* 2009 131, 2706-2712; Przybyla D et al. *J. Am. Chem. Soc.* 2013, 135, 3418-3422; Kojima C et al. *J. Am. Chem. Soc.* 2009 131, 30652-6053; Slatter D et al. *Peptides* 2012 36, 86-93; Kar et al. *Journal of Biological Chemistry* 2006 vol 281, no. 44 33283-33290. To obtain these specific forms, various approaches have been used, based notably on the use of metals or salts, on the addition of cysteine (disulfide bridges) or aromatic amino acids in the peptide sequence or on the ratio between amino acids of different nature (polar, apolar, acidic, basic).

Apart from the collagens, the proteins entering into the formulation of the preparation of the present invention may be recombinant proteins such as those described in the international patent application WO 2010/034718. These recombinant proteins derived from collagen are capable of inducing platelet aggregation in an equivalent manner to native collagen. Other proteins useful in the present invention and derived from collagen are those described in the European patent application EP 2013/071816. These proteins are capable of binding to Willebrand factor, a binding that is implicated in the initial adhesion of platelets at the injured vascular site.

In this way, the proteins entering into the formulation of the preparations of the present invention may be chosen from among native collagens, such as collagens of types I and III, or recombinant proteins whose sequence includes at least one polypeptide chosen from among:
- the polypeptide of sequence ID No. 1;
- a polypeptide having sequences formed from the repetition of GXY triplets, where G designates glycine and X and Y designate any amino acid, repeated n times with n greater than or equal to 2;
- the polypeptide having the sequence from position 25 to 184 of sequence ID No. 1; or
- a polypeptide having at least 70% identity along its entire length with the polypeptide of sequence ID No. 1 or with the polypeptide having the sequence from position 25 to 184 of sequence ID No. 1.

Furthermore, natural or synthetic peptides or polypeptides that have a sequence with a glycine every 3 amino acids may be considered as collagen derivatives (An B et al. *Frontiers in chemistry*. 2014 June; 2 article 40). This primary structure of the chain induces a confirmation of the peptide chain similar to that of collagen in the presence of amino acids (e.g. cysteine) or peptide sequences enabling the formation of multimeric structures (e.g. the trimerization domains of MBL [mannose-binding lectin] proteins).

The peptide from position 1 to position 24 of sequence ID No. 1 corresponds to the signal peptide enabling the secretion of the recombinant protein by a host cell. This signal peptide may be absent or replaced by another signal peptide according to techniques that are well known to the person skilled in the art. The person skilled in the art will be able to choose the homologous or heterologous signal peptide that is appropriate for the expression and secretion of the polypeptides in the various prokaryotic or eukaryotic systems of expression. Preferably, the polypeptides are produced in eukaryotic cells or organisms, and in particular in mammalian cells. In a particular embodiment of the invention, the polypeptides include a signal peptide enabling their secretion into the extracellular medium. In another embodiment, the mature polypeptide is obtained after cleavage of the signal peptide.

In certain embodiments, the sequence of the recombinant proteins includes at least one polypeptide containing the following peptide sequences:
- $GX_1X_2GER$, in which $X_1$ and $X_2$ represent independently an amino acid chosen from among A, R, N, D, Q, E, G, H, I, K, M, F, P, S, T, W, Y, V and O;
- $(GPX_3)_n$, with n between 4 and 10 and $X_3$ representing P or O; and
- $GPRGQX_4GVMGFX_5$, where $X_4$ and $X_5$ represent independently P or O.

P represents proline and O represents hydroxyproline.

In certain embodiments, the sequence of the recombinant proteins includes at least one polypeptide containing the following peptide sequences:
- GAPGER,
- KPGEPGPK,
- $(GPP)_n$, with n between 4 and 10,
- RGD.

In this way, the recombinant proteins include:
(a) peptide sequences having at least one repetition of 4 GPO triplets;
(b) peptide sequences having a binding activity to the various platelet receptors and presence in the native sequence of collagens; and
(c) binding sequences formed from the repetition of GXY triplets between the sequences (a) and (b) in which G designates glycine and X and Y designate any amino acid.

The recombinant proteins entering into the formulation of the preparations of the present invention may present a sequence including at least one polypeptide having at least 70% identity along its entire length with the polypeptide of sequence ID No. 1 or with the polypeptide having the sequence from position 25 to 184 of sequence ID No. 1. In certain embodiments, the polypeptides present at least 70%, 80%, 90%, 95%, 98% and preferably at least 99% identity with the polypeptide of sequence ID No. 1. The percentage identity designates the percentage of identical amino acids (amino acids that are invariant or unchanged between the two sequences). These polypeptides may present a deletion, an addition or a substitution of at least one amino acid with respect to the polypeptide of sequence ID No. 1.

The methods of measurement of the percentage identity between polypeptides are known to the person skilled in the art. Vector NTi 9.1.0, alignment program AlignX (Clustal W algorithm) (Invitrogen INFORMAX, http://www.invitrogen.com) may be used. Preferably, the default parameters are used.

The recombinant proteins may be produced by bacteria and mammalian cells by methods well known to the person skilled in the art, in particular those described in WO 2010/034718 and EP 2013/071816.

In certain embodiments, the proteins are also capable of binding to collagen presence at the injured vascular sites, notably through the presence in the sequence of a GPO sequence repeated n times, with n=3-10.

In certain embodiments, the proteins may be PEGylated or PASylated (addition of the amino acids proline, alanine and serine n times).

The peptides entering into the formulation of the preparations of the present invention may be those described above. In this way, the peptides may be chosen from among:

- the polypeptide of sequence ID No. 1;
- a polypeptide having sequences formed from the repetition of GXY triplets, where G designates glycine and X and Y designate any amino acid, repeated n times with n greater than or equal to 2;
- the polypeptide having the sequence from position 25 to 184 of sequence ID No. 1; or
- a polypeptide having at least 70% identity along its entire length with the polypeptide of sequence ID No. 1 or with the polypeptide having the sequence from position 25 to 184 of sequence ID No. 1.

The polypeptides are isolated or purified from the natural environment. The polypeptides may be prepared by means of various processes. These processes are notably the production of recombinant polypeptides by appropriate host cells and their later purification, production by chemical synthesis, or finally a combination of these different approaches. These various production processes are well known to the person skilled in the art. Preferably, the polypeptides are produced by prokaryotic or eukaryotic recombinant cells. In this way, the polypeptides may be produced in bacteria or in mammalian cells.

In certain embodiments of the invention, the polypeptides are glycosylated. The polypeptide of sequence ID No. 1 notably has O-glycosylation sites at the lysine amino acids present at positions 102 and 141 (in position three of a GXY triplet). In a preferred embodiment, the asparagine residue at position 93 of the polypeptide of sequence ID No. 1 is glycosylated.

Proteins in Fibrillar Form

The proteins entering into the formulation of the injectable preparations according to the present invention may be structured in the form of fibrils with a length of less than 10 μm. The fibrillar forms that include fibres with a length greater than 10 μm, and which may reach several micrometers in length, are not compatible with injection into the bloodstream.

The length of a fibril may be measured by methods well known to the person skilled in the art, in particular by microscopy such as atomic force microscopy (AFM).

Particles

The particles entering into the formulation of the preparations of the present invention may include, or consist of, proteins or peptides inducing the adhesion and activation of platelets or their aggregation. The proteins and peptides are as described above.

In certain embodiments, the particles may be obtained by adhesion of proteins or peptides to a support. In this way, the particles entering into the formulation of the preparations of the present invention include supports onto which are adhered proteins or peptides inducing the adhesion, activation or aggregation of platelets.

The supports may be organic or inorganic microparticles. Examples of microparticles include albumin, lipids, metals such as gold, titanium, iron, silver, or oxides thereof, graphene, silica, or polymers.

The adhesion of proteins or peptides onto the supports may be made by covalent bonding through functional groups present on the surface of the particle, or through a bifunctional spacer or a bifunctional polymer. The bifunctional spacer or the bifunctional polymer enable the functionalization of microparticles. At one end it presents a functional group that enables it to graft itself covalently to the surface of the microparticles and, at the other end, it presents a functional group enabling it to graft itself covalently to the proteins or peptides.

Preferably, the bifunctional polymer is a heterobifunctional polymer. The presence of two different functional groups enables undesired couplings, such as the attachment of both ends of the polymer to the microparticles, to be limited. Preferably, the affinity between the terminal functional groups of the polymer is also weak so as to limit the self-condensation of the polymer by the interaction between these two ends.

Various types of bifunctional polymer may be used to functionalize the microparticles. In this way, the bifunctional polymers may be chosen from among polyethylene glycol (PEG), poly(lactic-co-glycolic acid) (PLGA), poly(caprolactone) (PLCL), poly(lactic acid) (PLA), glycolide polymers (PGA), chitosan, dextran, etc. Preferably, the polymer is a bifunctional polyethylene glycol, preferably heterobifunctional. The molecular mass of the polymer generally varies from 500 Da to 10,000 Da, preferably 2000-8000 Da, more preferably around 5000 Da. The molecular mass of the polymer is typically chosen so that, when a protein or peptide is attached to the microparticle through the bifunctional polymer, the polymer chain has a sufficient length for the properties of the protein or peptide not to be affected by the presence of the microparticle.

In certain embodiments, the particles may be obtained by self-assembly of proteins or peptides. In such embodiments, the particles do not include a support but consist solely of the proteins or peptides. The self-assembly may be carried out by different methods, such as by coacervation or by aggregation, for example by precipitation, concentration, addition of metals or salts, or variation of temperature.

The particles of the present invention may have a mean diameter ranging from 0.05 μm to 6 μm, or from 1 μm to 5 μm, or from 2 μm to 4 μm, as measured by dynamic light scattering (DLS). Advantageously, the mean diameter of the particles of the present invention may be between 0.02 μm and 0.05 μm, for example between 0.025 μm and 0.045 μm, or for example equal to 0.035 μm.

When the particles include or consist of recombinant proteins whose sequence includes at least one polypeptide from among:
- the polypeptide of sequence ID No. 1;
- the polypeptide having the sequence from position 25 to 184 of sequence ID No. 1; or
- a polypeptide having at least 70% identity along its entire length with the polypeptide of sequence ID No. 1 or with the polypeptide having the sequence from position 25 to 184 of sequence ID No. 1;

and when they present a mean diameter greater than 2 μm as measured by DLS, they are capable of inducing adhesion, activation and aggregation of platelets. This effect is also found for molecules whose mean diameter is lower than 2 μm, for example between 0.02 μm and 1 μm, between 0.05 μm and 0.5 μm, or between 0.1 μm and 0.3 μm.

Pharmaceutically Acceptable Vehicle or Excipient

Pharmaceutically acceptable vehicles or excipients according to the invention, i.e. vehicles or excipients whose administration to an individual is not accompanied by significant adverse effects, are well known to the person skilled in the art.

Examples of pharmaceutically acceptable excipients or vehicles include, but are not limited to, solvents, glidants, suspension agents, solubilization agents, stabilizers, preservatives, buffers, antioxidants and chelating agents.

The injectable preparations according to the present invention may be prepared according to methods well known to the person skilled in the art.

The injectable preparations according to the present invention are capable of controlling bleeding by platelet activation and/or by substituting for platelets in the case of hemorrhagic syndromes.

The present invention relates therefore to methods for the treatment of hemorrhage that include the administration by injection of an effective quantity of a preparation as defined above into the bloodstream of an individual.

It is clear therefore that, in the context of the present invention, an "injection" is synonymous with a systemic administration, sometimes called general administration, of the product of the invention to a patient.

Finally, the present invention relates to the use of a preparation as defined above for the preparation of a medicinal product to treat hemorrhage.

EXAMPLES

Production of a Collagen and Self-Assembly into Particles (Method of Determination of the Size of the Particles by DLS)

A 3-week pre-culture of CHO—S cells (Invitrogen) is carried out before the transfection. The cells are maintained in a medium specific for CHO cells (Power-CHO, EXCEL 302, proCHO4, proCHO5, etc.) complemented with 4 mM L-glutamine (Lonza) and 1×proHT (Lonza) in a 125 mL shake flask under agitation (80 rpm) in an incubator at 37° C. with 5% $CO_2$. Two days before the transfection, the cells are seeded at $5\times10^5$ viable cells/mL by a complete change of medium and cultivated in 12.5 mL of complemented medium specific for CHO cells in a 125 mL shake flask.

On the day of the transfection, $5\times10^6$ viable cells are separated by centrifugation (5 min at 1000 g), then taken up in 5 mL of RPMI medium (Lonza) complemented with 4 mM L-glutamine (Lonza) and 1×proHT (Lonza). 4 mL of suspension are then divided between four 25 mL shake flasks (1 mL per flask) containing 9 mL complemented RPMI medium ($1\times10^6$ viable cells per shake flask). The CHO—S cells are then transfected with the vector containing the sequence coding for the polypeptide of sequence ID No. 1 described previously. A positive transfection control is carried out by transfecting the cells with the pMAX-GFP vector and two negative transfection controls are carried out by transfecting the cells with a vector not carrying genes for resistance and by not performing any treatment. The transfection is carried out using the transfection agent Fecturine (PolyPlus Transfection) or any other appropriate transfection agent and according to the optimized commercial protocol of the product. For Fecturine, the chosen transfection conditions are 6 μg DNA for 12 μL Fecturine (DNA/transfection agent ratio=½) for $10^6$ viable cells. The person skilled in the art will know how to define the most appropriate transfection agents for a transitory transfection or for a stable transfection. Whether the mode of transfection is transitory or stable, the cells are incubated in the presence of the transfection complexes under static conditions at 37° C. and 5% $CO_2$. Four hours after transfection, the cells are resuspended in complemented medium specific for CHO cells and returned to agitated conditions. 24 hours after transfection, a measurement of the transfection efficacy is carried out on aliquots of the positive and negative transfection controls by flow cytometry.

For the production of the polypeptide of sequence ID No. 1 in the transitory mode, an initial sample of supernatant is taken at D+3 (D0 corresponding to the day of transfection), then the culture is stopped at D+5. The culture supernatant containing the polypeptide of sequence ID No. 1 secreted by cells is recovered after centrifugation at 3000 g for 10 minutes, so enabling the elimination of cells and cell debris, then frozen at −20° C.

For the production of the polypeptide of sequence ID No. 1 in the stable mode, a cell count is carried out 48 hours after transfection. All the cells are then centrifuged at 1000 g for 5 minutes then seeded at $3\times10^5$ viable cells/mL in complemented medium specific for CHO cells+700 μg/mL geneticin (G418 Merck) (selection pressure). The cells are then maintained three times a week by seeding all the cells in a final volume of 12.5 mL complete medium+700 μg/mL G418 in 125 mL shake flasks. A reduction in cell concentration and/or cell viability is observed in the first week of culture under selection pressure. The cell viability increases again after 2-3 weeks under selection pressure, but only for the cells transfected with the vector containing sequence coding for the polypeptide of sequence ID No. 1 or the empty vector. The viability of the non-transfected cells continues to drop until it becomes zero. Once the culture reaches more than 95% viability, cryo-conservation at $5\times10^6$ viable cells/ampoule (in 10 ampoules) is carried out. The cells are frozen in complemented medium specific for CHO cells+10% DMSO.

To produce the polypeptide of sequence ID No. 1, the cells that have been genetically modified to produce the polypeptide of sequence ID No. 1 are thawed and maintained in an appropriate medium. The cells are placed in 12.5 mL of final medium and placed in a 125 mL shake flask in a Kühner LabTherm® agitator at 80 rpm, regulated at 5% $CO_2$ and with a humidity between 40% and 80%. The cells are maintained at $3\times10^5$ viable cells/mL for one or two weeks. The cells are then amplified so as to have the quantity necessary to carry out production. The amplification consists of maintaining cells in larger volumes at each change of medium so as to keep all the cells at a viable concentration.

Once the quantity of cells necessary for production is obtained, production can be launched. The cells are seeded at $3\times10^5$ viable cells/mL. The production can be carried out in various equipment: shake flask placed in a Kühner LabTherm® agitator, Cultibag RM 20/50® (Sartorius), CellReady® (Merck Millipore), BioBundle® (Applikon) and other equivalents equipment of the same or larger scale. The subculture is carried out for 5 days or more, 10 days at the most, according to the culture conditions. The production parameters, cell concentration and cell viability are monitored every day. During production, components such as amino acids, vitamins, glucose, or any other element having an interest for the production or for the cells may be added. In this case, the culture is "fed-batch" or "semi-continuous", which enables the cells to be cultivated from maximum of 21 days. If no compound is added during the culture, it is a "batch" or "discontinuous" culture.

The purification of the polypeptide of sequence ID No. 1 may be carried out for example using a purification label such as the tag-6(His) present in its sequence. In this way, the cells and cell debris present in the medium containing the polypeptide of sequence ID No. 1 are eliminated by centrifugation or depth filtration (Merck Millipore POD Millistak+®) or any other type of equipment support) or tangential filtration on a membrane with a cut-off of 0.2 µm. The supernatant so obtained is purified by affinity chromatography on a column collated with a metal such as nickel, cobalt, zinc or copper. So as to favor the attachment of the polypeptide of sequence ID No. 1, a buffer solution containing 0-50 mM imidazole, 0-500 mM NaCl, 5-20 mM ($Na_2HPO_4.2H_2O$) and 5-20 mM ($NaH_2PO_4$—$H_2O$) is added to the supernatant and adjusted to a pH between 7 and 8. The evolution of the polypeptide according to the invention is either carried out by gradient using a mixture of two buffer solutions (buffer 1: 500 mM imidazole, 500 mM NaCl, 10 mM ($Na_2HPO_4.2H_2O$) and 10 mM ($NaH_2PO_4$—$H_2O$); buffer 2: 20 mM imidazole, 500 mM NaCl, 10 mM ($Na_2HPO_4.2H_2O$) and 10 mM ($NaH_2PO_4$—$H_2O$), or isocratically with a buffer solution containing 50-500 mM imidazole, 0-500 mM NaCl, 5-10 mM ($Na_2HPO_4.2H_2O$) and 5-10 mM ($NaH_2PO_4$—$H_2O$). Other purification steps may be added so as to improve the purity of the polypeptide of sequence ID No. 1. These may be filtrations, ion-exchange chromatography, affinity chromatography, hydrophobic interaction chromatography, size-exclusion chromatography or any other type of chromatography.

The elution fractions of interest are placed to migrate on an electrophoresis gel under native conditions and stained with Coomassie blue before being collected according to their profile and dialyzed in water or phosphate buffer or any other buffer solution appropriate for the storage of the polypeptide according to the invention. The concentration of polypeptide is determined by the Sircol® kit (TebuBio) according to the manufacturers instructions or by the Bradford test or any other test appropriate for the quantification of the polypeptide of sequence ID No. 1.

The polypeptide of sequence ID No. 1 is concentrated multiple times (50 times) with respect to its initial volume by ultrafiltration, enabling a protein concentration to be reached that is sufficient to induce the self-assembly of the polypeptide of sequence ID No. 1 and the formation of particles. The protein extract containing the polypeptide sequence ID No. 1 is concentrated in this way on ultrafiltration columns having a cut-off of 10,000 Da (Vivaspin 4, Sartorius) by repeated centrifugations carried out at 4° C. and 4000 rpm. Once the solutions been concentrated, a measurement of the size of the particles so formed is carried out by the dynamic light scattering (DLS) technique using a Malvern Zetasizer nano instrument. The DLS measurement is a nondestructive spectroscopic analysis technique that enables the size of particles in suspension in a liquid to be measured; it is particularly appropriate for the measurement of the self-assembly or aggregation of proteins such as the polypeptide of sequence ID No. 1.

FIG. 1 shows a characteristic result of the measurement of the size of the particles by DLS after concentration by a factor of 50 of a protein extract of the polypeptide of sequence ID No. 1. A series of peaks is observed, corresponding to the different sizes of particle present in the solution. Three peaks are prominent: they correspond to particle sizes of 1.25 µm, 3 µm and 5.5 µm. So as to link the biological activity of the polypeptide of sequence ID No. 1 to the size of the particles so generated, hydrochloric acid is added to the solution to a final concentration of 20 mM. The three peaks previously measured then disappear, and two peaks at about 500 nm and 1.8 µm appear. Visually, the fraction is observed to "clear", passing from a grainy appearance to a translucent appearance.

Measurement of the Willebrand Factor Binding Activity as a Function of Particle Size The preparation based on the polypeptide of sequence ID No. 1 in the form of particles has the ability to bind Willebrand factor. The measurement of the Willebrand factor binding activity of the polypeptide of sequence ID No. 1 by the ELISA technique is carried out in 96-well plates (Nunc Maxisorp). For this, a volume of 100 µL of a solution containing the polypeptide at 2 µg/mL in phosphate buffer or any other appropriate buffer solution is added to each well and incubated for 18-20 h at 22° C. After three washes with 200 µL PBS-0.05% Tween, 200 µL of a 1% solution of BSA in phosphate buffer (Euromedex, filtered through 0.45 µm) are added to each well and incubated for two hours at ambient temperature (22° C.). After three washes with 200 µL PBS-0.05% Tween, 100 µL of various concentrations (expressed in IU/dL) of purified Willebrand factor (Wilfactin 100 IU/mL, LFB) and/or patient's plasma diluted in phosphate buffer or any other appropriate buffer solution is incubated for 1 h 30 min at ambient temperature (22° C.). After three more washes, 100 µL of a solution containing a primary anti-vWF antibody coupled to horseradish peroxidase (Rabbit anti-human VWF/HRP, DAKO) diluted to 1:8000 in phosphate buffer or any other appropriate buffer solution is incubated for one hour at 22° C.; four washes are then performed as described above. 125 µL tetramethylbenzidine solution (TMB, Sigma) is then added as a substrate for the peroxidase; the plates are incubated 10-45 minutes maximum in darkness. The reaction is quenched by the addition of 125 µL 2N HCL (Sigma). The absorbance at 450 nm is measured without delay in a spectrophotometer (Wallacvictor 3). A blank is performed by replacing the purified vWF or the plasma by phosphate buffer or any other appropriate buffer solution.

Figure 2:
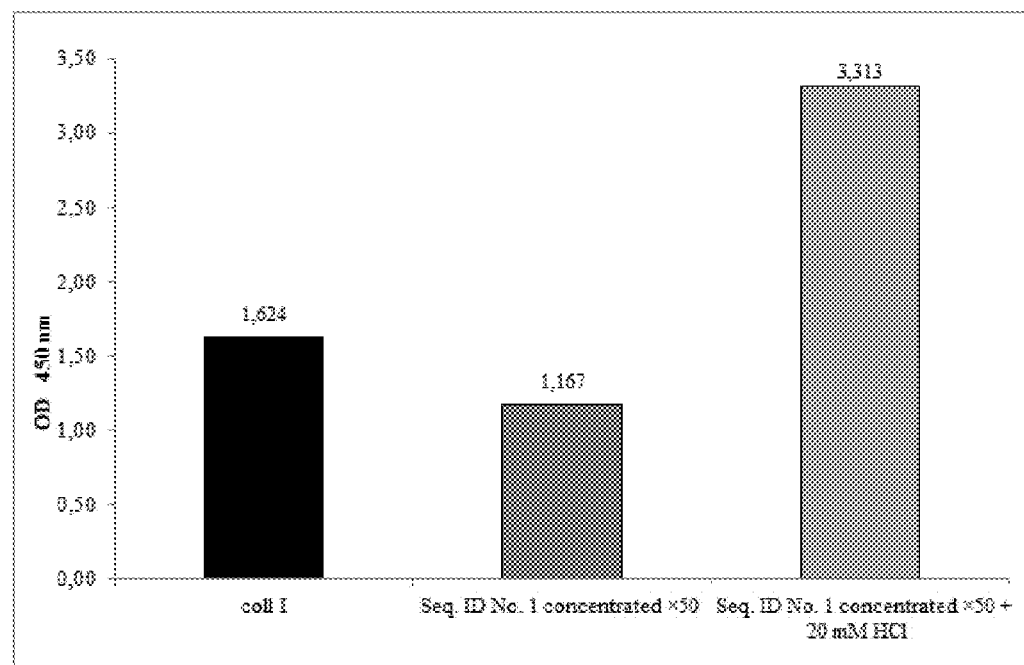
FIG. 2 shows a result obtained by ELISA of the binding of purified Willebrand factor (Willfactin, LFB), used at a final concentration of 2 IU/dL, to the polypeptides of sequence ID No. 1 in the form of particles of different sizes, used at a final concentration of 2 μg/mL and to type I collagen (SIRCOL collagen, positive control) used at 10 μg/mL.
Figure 3:
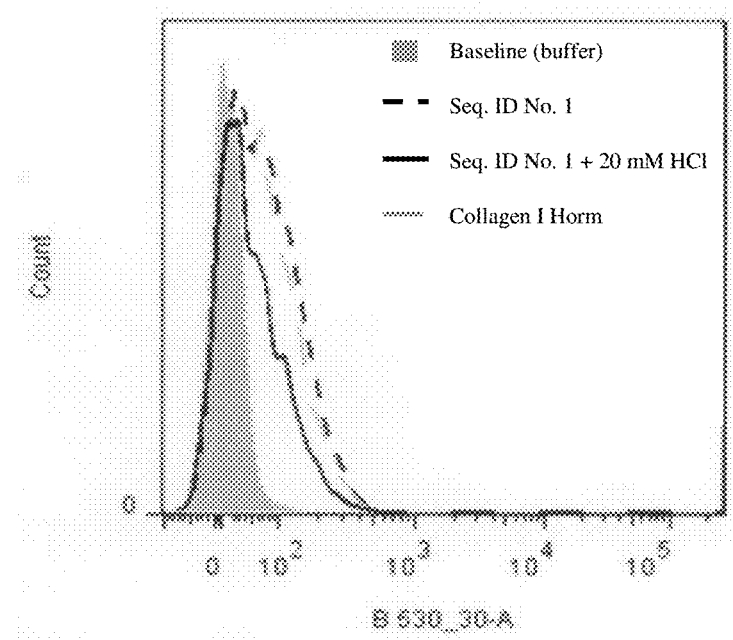
FIG. 3A represents a typical profile of the expression of P-selectin on the surface of platelets for the polypeptide of sequence ID No. 1 and for type I collagen (Norm), obtained by flow cytometry
FIG. 3B represents the mean fluorescence intensities obtained for various agonists.
Figure 4:
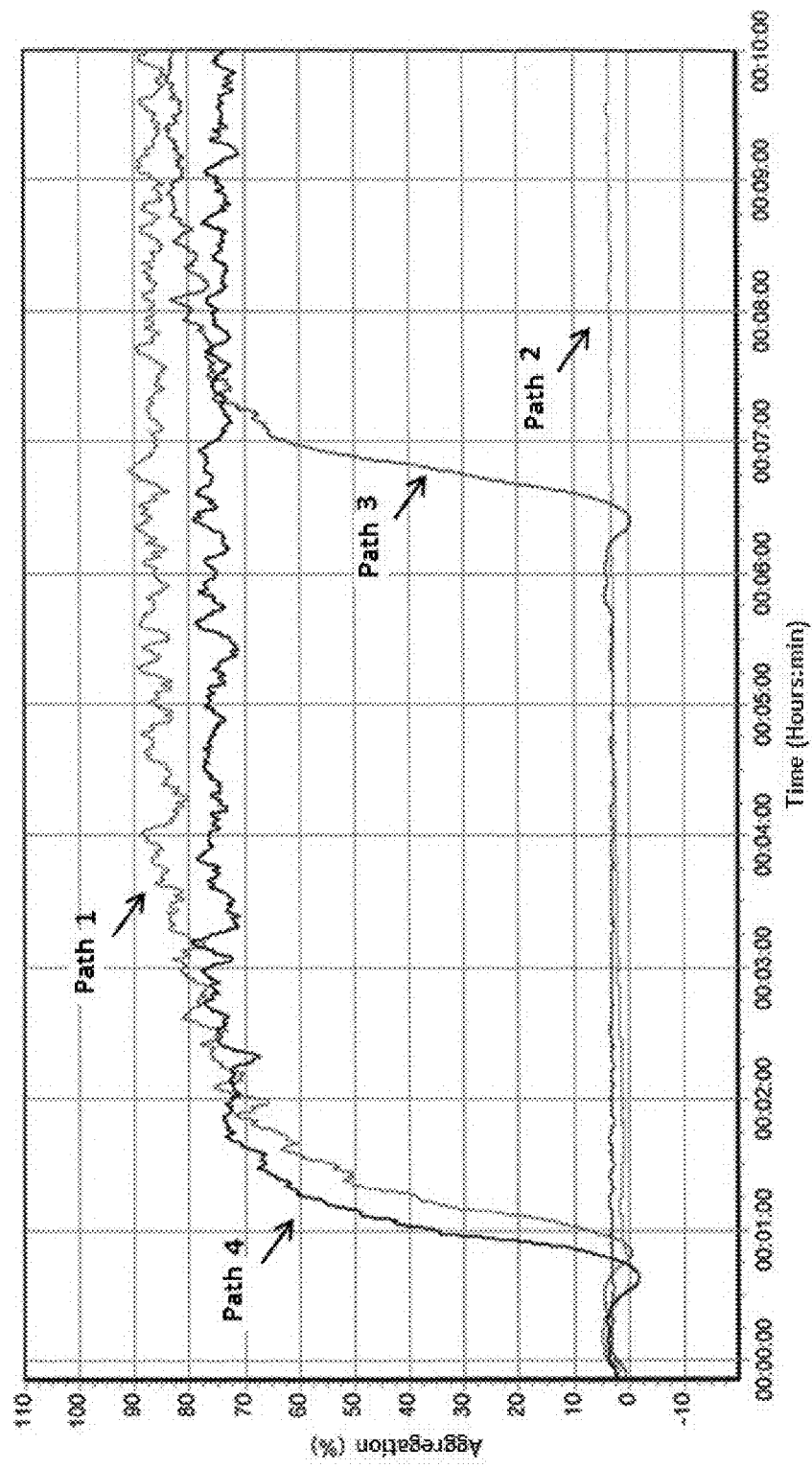
FIG. 4 shows an aggregation result obtained with the polypeptide of sequence ID No. 1 in the form of particles.

FIG. 2 shows a result obtained by ELISA of the binding of purified Willebrand factor (Willfactin, LFB), used at a final concentration of 2 IU/dL, to the polypeptides of sequence ID No. 1 in the form of particles of different sizes, used at a final concentration of 2 µg/mL and to type I collagen (SIRCOL collagen, positive control) used at 10 µg/mL.

The results show that the polypeptide of sequence ID No. 1, made up of a majority of particles larger than 2 µm, is capable of binding Willebrand factor in an equivalent manner to type I collagen. The Willebrand factor binding activity is greatly increased when the polypeptide of sequence ID No. 1 is in the form of particles smaller than 2 µm. This latter result suggests that the self-assembly of the polypeptide of sequence ID No. 1 into larger particles reduces the number of Willebrand factor recognition sites, which are probably "hidden" on the inside of larger particles. This result shows that a polypeptide of sequence ID No. 1 structured into particles between 1 μm and 5 μm in size is indeed capable of binding Willebrand factor.

Measurement of the Surface Expression of P-Selectin Induced by the Collagen as a Function of the Size of the Particles The preparation based on the polypeptide of sequence ID No. 1 in the form of particles has the ability to induce the activation of platelets. This activation can be determined in whole blood by measuring the platelet surface expression of P-selectin by flow cytometry. In resting platelets, P-selectin is stored in granules called alpha grains. When the platelets are activated by different agonists, the P-selectin is released from these granules and is detectable on the platelet surface.

A blood sample is taken in a citrate tube (BD Vacutainer, BD Biosciences) then stabilized for one hour before being used. In glass tubes, 50 μL blood is added to 50 μL phosphate buffer solution containing the polypeptide of sequence ID No. 1 at a concentration of 50 μg/mL (final concentration 25 μg/mL); the mixture is incubated for 10 minutes at ambient temperature.

The reaction is then stabilized by addition of 500 μL phosphate buffer to each tube. In cytometry tubes, 20 μL of the previously described reaction mixture is then added to 20 μL of a solution containing either primary anti-CD62P antibodies coupled to FITC (FITC Mouse Anti-Human CD62P, BD Biosciences) or isotypical control antibodies coupled to FITC (FITC Mouse IgG1 κ isotype control, BD Biosciences) and is incubated for 10 minutes at ambient temperature in darkness. 2 mL phosphate buffer is then added to each tube. The mean fluorescence intensity (MFI) is measured at 520 nm without delay using a flow cytometer (LSRII, BD Biosciences). A negative control is carried out by replacing the polypeptide of sequence ID No. 1 by phosphate buffer. Two positive controls are carried out by replacing the polypeptide of sequence ID No. 1 by the TRAP thrombin-derived platelet activator (human clinical diagnostic kit: PLT Gp/Receptors Kit, Biocytex) or the ionophore activator A23187 (Calbiochem, Merck; *Streptomyces chartreusensis*). A reference is performed by replacing the polypeptide by type I collagen (Norm) used at 50 μg/mL.

FIG. 3A corresponds to a representation of a typical profile of the expression of P-selectin on the surface of platelets for the polypeptide of sequence ID No. 1 and for type I collagen (Norm), obtained by flow cytometry The table in FIG. 3B shows the mean fluorescence intensities obtained for various agonists. The TRAP and the calcium ionophore are used as positive activation controls.

The polypeptide of sequence ID No. 1 with particle size greater than 2 μm is capable of inducing platelet activation characterized by the surface expression of P-selectin. This activation is equivalent to that induced by fibrillar type I collagen (fibres larger than 1 μm) used at the same concentration. The polypeptide of sequence ID No. 1 with particle size smaller than 2 μm (sequence ID No. 1+20 mM HCl) is also capable of inducing the expression of P-selectin and therefore the activation of platelets, but to a lesser extent (47.3 vs. 70.4 MFI).

Measurement of the Platelet Aggregation Induced by the Collagen as a Function of the Size of the Particles The preparation based on the polypeptide of sequence ID No. 1 in the form of particles has a pro-aggregant activity on human blood platelets detected with a thrombo-aggregometer (Soderel, Florange, France), according to the reference technique (Born, 1962). The platelet-rich plasma (PRP) is placed in contact with an agonist (10 μL in 290 μL of PRP) and the clearing of the medium (linked to the formation of aggregates) is monitored in real-time (aggregation curve). In the absence of platelet aggregation, the signal remains flat (the medium remains cloudy). It is possible to verify the presence or absence of aggregates by examining the tube at the end of the measurement. The evaluation of the platelet aggregation test response is carried out at 37° C. under continuous stirring (1000 rpm). The instrument is standardized as follows: 0% aggregation with platelet-rich plasma (preparation obtained by slow centrifugation and concentration, adjusted to $300\times10^9$/L) and 100% aggregation with platelet-poor plasma (preparation obtained by rapid centrifugation). The quality of the platelet preparations is validated by verifying the response to reference agonists (5 μM ADP and 1 μg/mL collagen) used for the development of anti-platelet treatments. A protein is considered pro-aggregant against when it is capable inducing an irreversible aggregation greater than 40%.

FIG. 4 shows an aggregation result obtained with the polypeptide of sequence ID No. 1 in the form of particles. Path 1 shows that the preparation of the polypeptide of sequence ID No. 1 with particle size greater than 2 μm is capable of inducing platelet aggregation in less than 1 minute and in a manner equivalent to Norm type I collagen (path 4), reference collagen in fibrillar form. On the contrary, the polypeptide of sequence ID No. 1 with particle size less than 2 μm is not capable of inducing platelet aggregation (path 2) even after 10 minutes. This absence of activity is not linked to the presence of 20 mM HCl in the solution, as path 3 shows normal platelet aggregation on stimulation by type I collagen, added after six minutes, in the presence of 20 mM HCl.

This result shows that the polypeptide of sequence ID No. 1 must be structured in the form of particles larger than 2 μm to obtain a pro-aggregant activity.

In conclusion, these different examples have shown that the polypeptide of sequence ID No. 1 is capable of structuring itself in the form of particles of between 1 μm and 6 μm in size, that these particles have the capacity to bind to Willebrand factor, to induce platelet activation (surface expression of P-selectin) and, only when a particle size is greater than 2 μm, to cause platelet aggregation.

Observation of the Structure of the Polypeptide of Sequence ID No. 1 in the Form of Particles Compared to Fibrillar Type I Collagen (Horm) by Various Microscopy Techniques.

There are various microscopy techniques that enable the macromolecular structure of a molecule to be visualized at different resolutions and scales. FIG. 5 shows images obtained with three microscopy techniques (transmission microscopy, scanning electron microscopy and atomic force microscopy) enabling the observation of the structure of collagen-type proteins.

Observation by transmission microscopy, the type I collagen or the polypeptide of sequence ID No. 1 is deposited on a glass slide over 2 hours at 37° C. before being observed using a ZEISS inverse phase-contrast microscope with a 60× objective. The images are obtained using a ZEISS AxioCam ICc 1 camera.

For observation by scanning electron microscopy, the surface chosen for the deposition is monocrystalline silicon (100). Being both a semiconductor and atomically flat, this is an obvious choice for the observation of collagens by this method. The sample preparation is carried out by placing a 10 μL drop of fibrillar type I collagen or polypeptide of sequence ID No. 1 concentrated to 200 μg·mL$^{-1}$ on the silicon surface for six hours. The surface is then rinsed with distilled water and dried under nitrogen. The dried surface is metalized by gold sputtering in an Edwards S150 sputter coater (25 mA current in 0.3 mPa argon atmosphere for 2 minutes). The sample surface is observed with a JEOL 6500F scanning electron microscope, with an emission potential of 20 keV and emission currents of 60 μA.

For observation by atomic force microscopy (AFM), the surface on which the type I collagen and the polypeptide of sequence ID No. 1 are observed is a polycrystalline gold surface (Au(111) terraces obtained by epitaxy on mica, PHASIS, ref. 20020022). The deposition took place ex situ at a concentration of 25 μg·mL$^{-1}$ underflow at a shear rate of 300 s$^{-1}$ over 30 minutes. To enable this flow functionalization, a PDMS microfluid cell is pressed onto the gold surface and the protein solution is brought to the surface through an ISMATEC IPC-4 peristaltic pump. The samples were observed with a Nanoscope IV Multimode atomic force microscope (Digital Instrument, Veeco Inc., Santa Barbara, Calif.) fitted with FESPA points (Bruker), with a spring constant k of N·m$^{-1}$, a resonance frequency f=50-100 kHz and a lever length L=200-250 μm. Acquisition is performed with the Bruker PeakForce QNM mode, a dynamic tapping mode enabling a low-noise acquisition on these biological samples. The scanning frequency is fixed at 1 Hz. The images obtained have been processed using the WSxM program so as to obtain a high resolution by applying the flatten and equalize functions.

Figure 5:
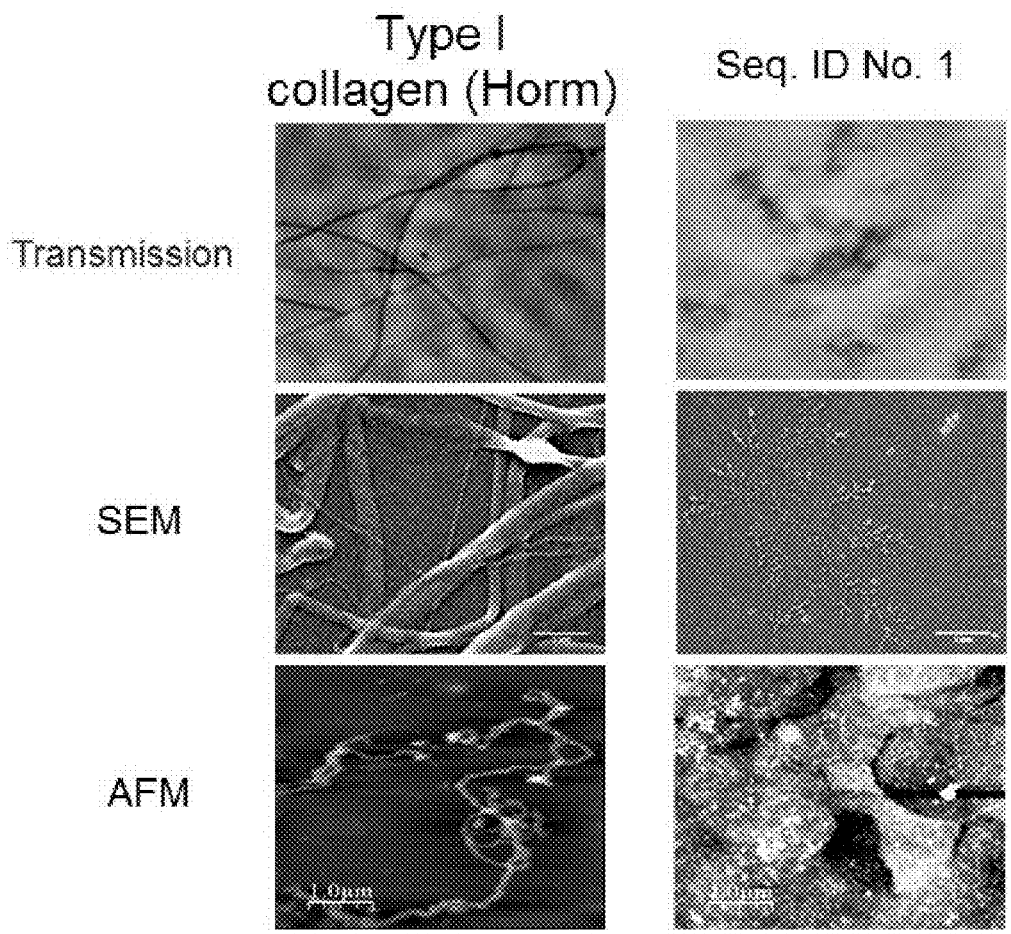
FIG. 5 shows the macromolecular structure of the polypeptide of sequence ID No. 1 in the form of particles compared to type I collagen (Norm) in fibrillar form, observed by various microscopy techniques.

The observations shown in FIG. 5 confirm the results obtained by DLS, indicating a structure in the form of particles for the polypeptide of sequence ID No. 1 compared to the fibrillar structure of the type I collagen. The size of the observed particles is of the order of a few tens of nanometers under the experimental condition used for their observation. Measurement of the Platelet Surface Expression of P Selectin after Injection of the Polypeptide of Sequence ID No. 1 in the Form of Particles and of Type I Collagen (Horm) in Fibrillar Form into Mice.

The preparation based on the polypeptide of sequence ID No. 1 in the form of particles or on fibrillar type I collagen has the ability ex vivo to induce the activation of platelets in whole blood, as shown by the platelet surface expression of P-selectin measured by flow cytometry. So as to validate that these preparations are indeed capable of inducing this same activation once injected into the bloodstream, a blood sample is taken in a citrate tube (BD Vacutainer, BD Biosciences) from mice 15 minutes after administration of 400 μg/kg type I collagen or of 2 mg/kg polypeptide of sequence ID No. 1 or at the moment of the first signs of an embolism (suffocation). 50 μL of blood is placed in glass tubes then stabilized with 250 μL phosphate buffer. In cytometry tubes, 20 μL of the previously described reaction mixture is then added to 20 μL of a solution containing either primary anti-CD62P antibodies coupled to FITC (FITC Mouse Anti-Human CD62P, BD Biosciences) or isotypical control antibodies coupled to FITC (FITC Mouse IgG1 κ isotype control, BD Biosciences) and is incubated for 10 minutes at ambient temperature in darkness. 2 mL phosphate buffer is then added to each tube. The mean fluorescence intensity (MFI) at 520 nm is measured without delay using a flow cytometer (LSRII, BD Biosciences).

Figure 6:
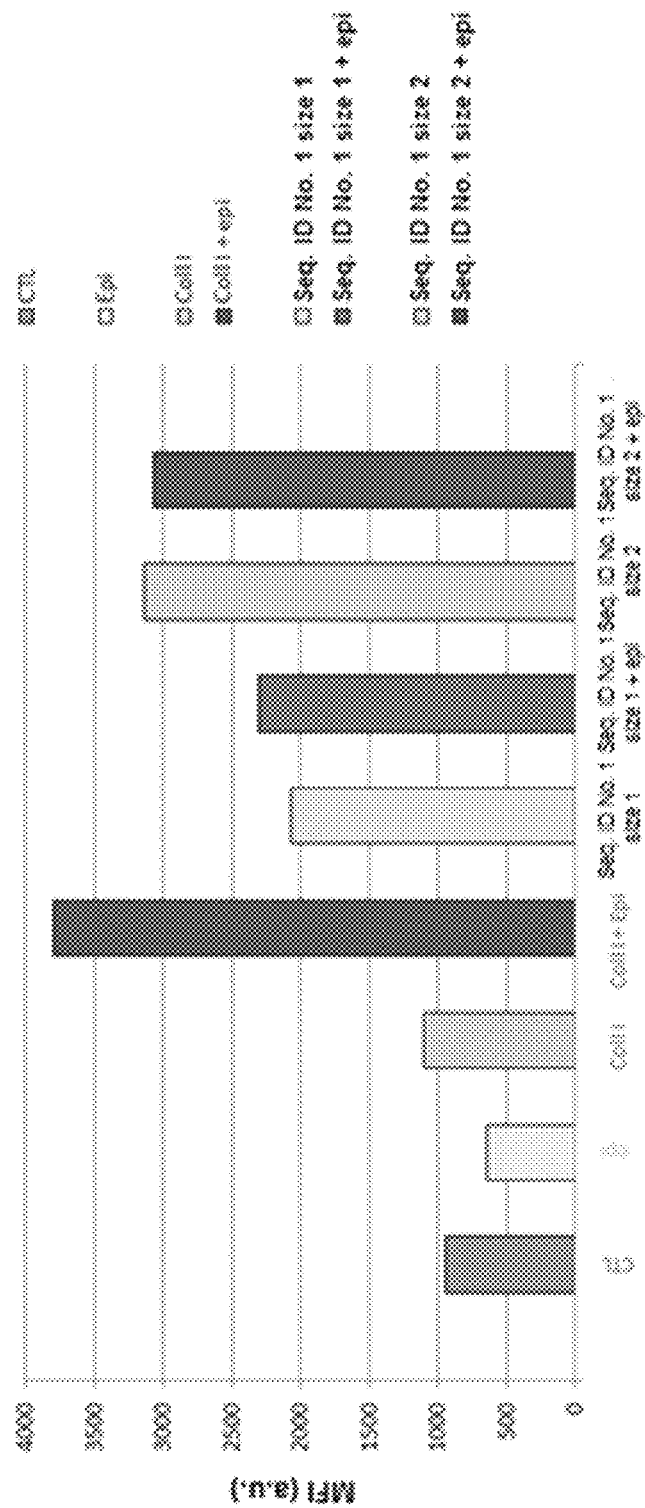
FIG. 6 represents the mean fluorescence intensities obtained by flow cytometry for the expression of P-selectin on the surface of platelets sampled after injection of the polypeptide of sequence ID No. 1 and of type I collagen (Norm) into mice.

FIG. 6 shows the platelet expression of P selectin measured from blood taken from mice after injection of fibrillar type I collagen and of the polypeptide of sequence ID No. 1, for two particle sizes, in the presence of epinephrine or not. It may be noted that the polypeptide of sequence ID No. 1 indeed induces the activation of platelets 15 minutes after its administration to mice or at the time of the first signs of an embolism (suffocation), whatever the particle size. This activation is not modulated by the concomitant administration of epinephrine, unlike fibrillar type I collagen, the activation by which is strongly increased by epinephrine. This result confirms that the polypeptide of sequence ID No. 1 is indeed capable of inducing the activation of platelets once administered into the bloodstream, as shown ex vivo. Measurement of the Thrombotic Risk Associated with the Injection into the Bloodstream of the Polypeptide of Sequence ID No. 1 in a Model of Pulmonary Embolism Induced in Mice The present invention describes the use of proteins or peptides derived from collagen for the treatment of hemorrhage by a mechanism depending on the activation of platelets. In order to determine whether, independently of the hemorrhagic context, the in vivo platelet activation induced by the injection of these proteins or peptides derived from collagen in the form of particles is associated with a risk of thrombosis, a model of pulmonary embolism induced in mice by administration of collagen and epinephrine has been used. The objective is to show that the platelet activation induced by the proteins or peptides derived from collagen of the present invention is not in itself harmful by inducing thrombosis once injected. In order to characterize the potentially thrombotic effect of this administration, a radioactive tracer that can be visualized by isotopic imagery (SPECT) has been used as an observational criterion in addition to that classically used in this model, which consists of measuring the time taken for the animal to die from pulmonary embolism. After intravenous injection, the macroaggregates of human albumin labelled with technetium-99m circulate in the bloodstream and enable scintigraphs to be taken of the lungs or of certain veins. If thrombotic foci exist, the normal pulmonary distribution of this tracer will be altered and the isotopic imagery will show the reduction or absence of tracer in the lungs.

Male SWISS mice of 25-30 g in weight are used for this pulmonary embolism model. The mice are kept under isoflurane anaesthesia throughout the duration of the experiment. Firstly, the two jugular veins are exposed before injecting the polypeptide of sequence ID No. 1 (1 mg/kg)/epinephrine (60 μg/kg) mixture or the fibrillar type I collagen (400 μg/kg)/epinephrine (60 μg/kg) mixture, in a final volume of 150 μL, into one of the veins. If a pulmonary embolism occurs, the mice start to suffocate and die within 10 minutes of the injection. It is considered that my surviving longer than 15 minutes have no pulmonary embolism. In order to perform a SPECT acquisition, the macroaggregates of human albumin labelled with technetium-99m (30 μCi per mouse in 100 μL final volume) are injected into the other jugular vein just after cardiac arrest for the mice with pulmonary embolism or after 15 minutes for the mice that survive. A scan then a 15-minute isotopic imagery acquisition are performed.

Figure 7:
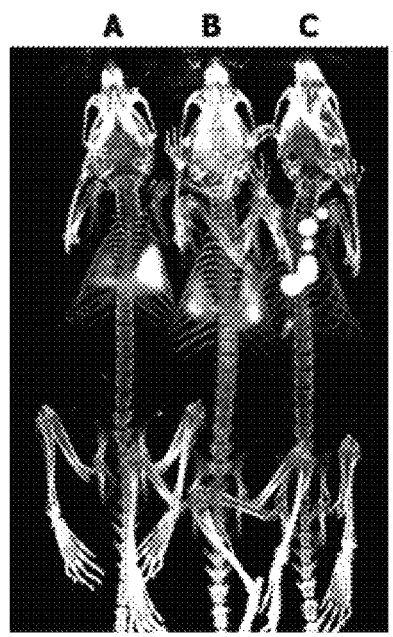
FIG. 7 shows the results of intravenous injection into mice, in the presence of epinephrine, of type I collagen (Norm) in fibrillar form and the polypeptide of sequence ID No. 1 in the form of particles in a model of induced pulmonary embolism in mice.

The table in FIG. 7A shows the results obtained after administration to mice of fibrillar type I collagen and of the polypeptide of sequence ID No. 1 in the form of particles in the presence of epinephrine in terms of the percentage of animals in which a pulmonary embolism was observed and the mean time for the appearance of this embolism. The results show that 100% of the animals are dead after 5 min 50 sec on average after injection of fibrillar type I collagen. On the contrary, no animal developed pulmonary embolism after injection of the polypeptide of sequence ID No. 1, even though it was used at a concentration 2.5 times higher (1 mg/kg vs 400 µg/kg). FIG. 7B shows the images obtained after injection of radiolabeled albumin macroaggregates that confirm the presence of massive pulmonary embolism in the mice injected with fibrillar type I collagen and the normal pulmonary distribution of tracer in the mice injected with the polypeptide of sequence ID No. 1, showing the absence of induced thrombosis.

This result confirms that, for the two collagen-type proteins having the same platelet-activating activity once injected into the bloodstream, only those in the form of particles may be used without risk of inducing thrombosis. Measurement of the Effect of Injection of the Polypeptide of Sequence ID No. 1 in a Model of Induced Bleeding from the Tail in Mice.

The results presented above confirm that the polypeptide of sequence ID No. 1 in the form of particles is indeed capable of inducing platelet activation once administered into the bloodstream of mice and that this activation has no thrombogenic effect, unlike fibrillar type I collagen. So as to validate that the injection of a protein or a peptide derived from collagen of the present invention into the bloodstream indeed enables the stopping of bleeding to be induced by a mechanism dependent on platelet activation, the effect on blood loss of the administration of the polypeptide of sequence ID No. 1 has been evaluated in a model of induced bleeding from the tail in mice.

Male SWISS mice of 25-30 g in weight are used for this model of bleeding from the tail. The mice are kept under isoflurane anaesthesia throughout the duration of the experiment. Firstly, one of the two jugular veins is exposed before injecting the different molecules diluted in phosphate buffer. The tail is sectioned 1.5 cm from the end so as to section the 3 arteries and the vein. The section is performed 10 minutes after injection of phosphate buffer (vehicle control) or of the polypeptide of sequence ID No. 1 (1.6 mg/kg) and 20 minutes after injection of heparin (anticoagulant, positive bleeding control, 60 III/kg). After section, the tail is placed in 50 mL physiological saline at 37° C. so as to collect the blood over 16 minutes without damaging the red blood cells. The tubes are left to settle over one hour at ambient temperature before being centrifuge for 15 minutes at 250 g. The supernatant is discarded and the pellet of red cells is taken up in 3 mL specific lysis buffer (8.3 g/L $NH_4Cl$, 1 g/L $KHCO_3$ and 37 mg/L EDTA). The optical density at 550 nm of 200 µL of lysate is read on a plate reader.

A calibration curve has been constructed in order to determine the volume of blood lost. For this, male SWISS mice of 25-30 g in weight were bled from the abdominal aorta. The blood was collected in citrate tubes to avoid coagulation. A range of blood volumes was made up in tubes containing 50 mL physiological saline. The treatment of the blood was then performed as described above (see FIG. 8A).

Figure 8:
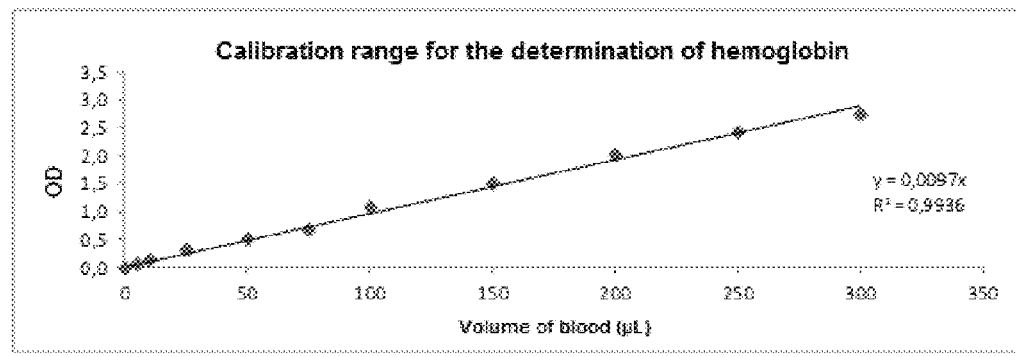
FIG. 8 shows the results of injection into mice of the polypeptide of sequence ID No. 1 in a model of induced bleeding from the tail in mice.
Figure 8:
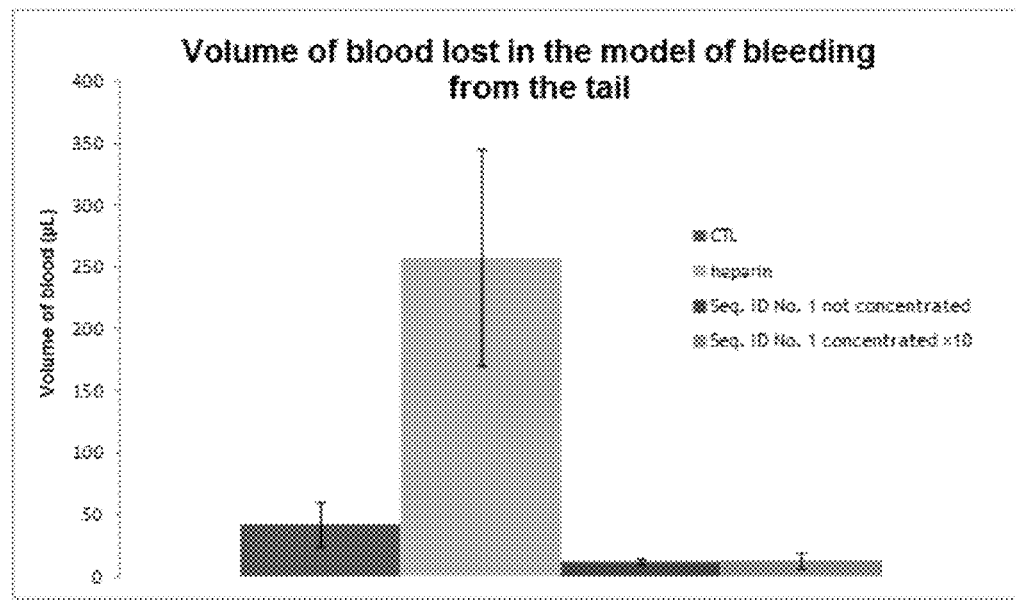

The results shown in FIG. 8B Confirm that the polypeptide of sequence ID No. 1, in the form of particles, is indeed capable of inducing the stopping of bleeding in this model, either in native form or in concentrated form. The mean volume loss before the stopping of bleeding in the presence of the polypeptide of sequence ID No. 1 is 11.6±2.4 µL (non-concentrated) and 12.6±6.1 µL (concentrated 10 times) vs 42±18.4 µL for untreated mice. The reduction in blood loss is therefore about 70% compared to the control mice. On the contrary, the blood loss in the presence of heparin is greatly increased, reaching a mean volume of blood lost of 257.9±87.5 µL. The increase in blood loss is therefore 514% compared to the control mice, validating the model.

REFERENCES

Spahn D et al. *Critical Care* 2013, 17:R76
Fries D. *Transfusion* 2013; 53:91S-95S
Lashof-Sullivan M et al. *Nanoscale* 2013, 5, 10719-10728
Modery-Pawlowski C et al. *Biomaterials* 2013: 516-541
Clementson K. *Thrombosis Research* 2012 129 220-224
Pires M and Chmielewski J. *J. Am. Chem. Soc.* 2009 131, 2706-2712
Przybyla D et al. *J. Am. Chem. Soc.* 2013, 135, 3418-3422
Kojima C et al. *J. Am. Chem. Soc.* 2009 131, 30652-6053
Slatter D et al. *Peptides* 2012 36, 86-93
Kar et al. *Journal of Biological Chemistry* 2006 vol 281, n °44 33283-33290
Mazepa M et al. *ATVB* 2013, 33(8):1747-52
Bonhomme F et al. *Eur J Intern Med.* 2014, 25(3):213-20
Beynon C et al. *Crit Care.* 2012 Jul. 26; 16(4):228
Jenkins D H et al. *Shock.* 2014 May; 41 Suppl 1:3-12
Murdock A D et al. *Shock.* 2014 May; 41 Suppl 1:62-9
An B et al. *Frontiers in chemistry.* 2014 June; 2 article 40

The invention claimed is:

1. An injectable preparation for use in the treatment of a hemorrhage comprising:
   particles comprising an isolated and aggregated protein or peptide inducing the adhesion and activation of platelets and having at least 90% identity with the polypeptide of SEQ ID NO:1; and
   at least one pharmaceutically acceptable vehicle or excipient.

2. The injectable preparation according to claim 1 wherein the protein or peptide has at least 95% identity with the polypeptide of SEQ ID NO:1.

3. The injectable preparation according to claim 1 wherein the protein or peptide has at least 99% identity with the polypeptide of SEQ ID NO:1.

4. The injectable preparation according to claim 1 wherein the particles are obtained by coacervation or self-assembly.

5. The injectable preparation according to claim 1 wherein the peptide or protein is adhered to supports.

6. The injectable preparation according to claim 5 wherein the supports are organic or inorganic microparticles.

7. The injectable preparation according to claim 6 wherein the peptide or protein is grafted onto the surface of the microparticles by covalent bonding.

8. The injectable preparation according to claim 6 wherein the microparticles comprise an albumin, a lipid, a metal, a metal oxide, graphene, or a polymer.

9. The injectable preparation according to claim 1 wherein the protein is pegylated or pasylated.

* * * * *

SEQUENCE LISTING

```
<160> NUMBER OF SEQ ID NOS: 1

<210> SEQ ID NO 1
<211> LENGTH: 184
<212> TYPE: PRT
<213> ORGANISM: Artificial Sequence
<220> FEATURE:
<223> OTHER INFORMATION: Synthetic Construct

<400> SEQUENCE: 1

Met Met Ser Phe Val Gln Lys Gly Ser Trp Leu Leu Leu Ala Leu Leu
1               5                   10                  15

His Pro Thr Ile Ile Leu Ala Gln Gly Arg Pro Gly Ala Pro Gly Glu
            20                  25                  30

Arg Gly Leu Pro Gly Pro Pro Gly Pro Arg Gly Ala Ala Gly Glu Pro
        35                  40                  45

Gly Arg Asp Gly Val Pro Gly Pro Gly Met Arg Gly Met Pro Gly
    50                  55                  60
```

-continued

```
Ser Pro Gly Gly Pro Gly Ser Asp Gly Lys Pro Gly Pro Pro Gly Ser
65                  70                  75                  80

Gln Gly Glu Ser Gly Arg Pro Gly Pro Pro Gly Glu Asn Gly Phe Pro
            85                  90                  95

Gly Glu Arg Gly Asp Ala Gly Ala Pro Gly Ala Pro Gly Pro Arg Gly
            100                 105                 110

Gln Pro Gly Val Met Gly Phe Pro Gly Asp Ala Gly Ala Pro Gly Ala
        115                 120                 125

Pro Gly Pro Arg Gly Gln Pro Gly Val Met Gly Phe Pro Gly Pro Pro
    130                 135                 140

Gly Pro Pro Gly Pro Pro Gly Pro Pro Gly Pro Pro Gly Pro Pro Gly
145                 150                 155                 160

Pro Pro Gly Pro Pro Gly Pro Pro Gly Pro Pro Gly Pro Arg Gly Asp
            165                 170                 175

Lys Gly Pro Pro Gly Pro Gly Ser
            180
```